(12) United States Patent
Mangione et al.

(10) Patent No.: US 6,485,714 B1
(45) Date of Patent: Nov. 26, 2002

(54) USE OF SALICYLIC ACID FOR REGULATING HYPERPIGMENTED SPOTS

(75) Inventors: Sherry A. Mangione, Williamsville; Jerome J. Schentag, Eggertsville, both of NY (US)

(73) Assignee: Sherry A. Bradford, Grand Island, NY (US)

(*) Notice: Subject to any disclaimer, the term of this patent is extended or adjusted under 35 U.S.C. 154(b) by 0 days.

(21) Appl. No.: 09/627,036

(22) Filed: Jul. 27, 2000

Related U.S. Application Data

(60) Provisional application No. 60/145,722, filed on Jul. 27, 1999.

(51) Int. Cl.[7] ............................ A61K 7/135; A61K 6/00; A61K 7/00
(52) U.S. Cl. ............................ 424/62; 424/401; 514/844; 514/846
(58) Field of Search ....................... 424/59, 401, 70.19, 424/70.22; 514/844

(56) References Cited

U.S. PATENT DOCUMENTS

| | | | | | |
|---|---|---|---|---|---|
| 5,573,759 A | * | 11/1996 | Blank | ........................... | 424/60 |
| 6,284,802 B1 | * | 9/2001 | Bissett et al. | ............... | 514/739 |

* cited by examiner

*Primary Examiner*—Thurman K. Page
*Assistant Examiner*—S. Howard
(74) *Attorney, Agent, or Firm*—Hodgson Russ LLP

(57) ABSTRACT

The present invention relates to a method for regulating hyperpigmented spots in mammalian skin comprising treating the skin with a safe and effective amount of salicylic acid and/or additional active component.

13 Claims, No Drawings

USE OF SALICYLIC ACID FOR REGULATING HYPERPIGMENTED SPOTS

CROSS-REFERENCE TO RELATED APPLICATION

This application claims priority based on provisional application Serial No. 60/145,722, filed Jul. 27, 1999.

FIELD OF THE INVENTION

The present invention relates to the treatment of hyperpigmented spots. More particularly, the present invention relates to the use of salicylic acid for treating hyperpigmented spots.

PRIOR ART

It is known to use salicylic acid for the treatment of acne. This is disclosed in U.S. Pat. Nos. 4,891,277 and 4,891,228 to Thaman et al., the disclosures of which are incorporated herein. Further, salicylic acid has been used for the removal of wart, corns and calluses; for the treatment of psoriasis, seborrheic dermatitis and dandruff; and for the topical treatment of ringworm infection. A listing of commercially available products containing salicylic acid can be found in the Physician's Desk Reference, 45th Edition, 1991, page 323. However, these prior art uses of salicylic acid have generally involved short term treatments in which relatively large doses of the acid are applied (i.e., sufficient to cause significant irritation and often peeling) in order to obtain a cure or treatment of the particular condition, such as removal of comedones, as opposed to persistent treatment of hyperpigmented spots.

SUMMARY OF THE INVENTION

The present invention relates to a method for regulating hyperpigmented spots in mammalian skin comprising chronic treatment of the skin with a safe and effective amount of salicylic acid.

DETAILED DESCRIPTION OF THE PREFERRED EMBODIMENT

As used herein, "alkyl" means an unsubstituted carbon-containing chain which may be straight, branched or cyclic, preferably straight or branched, more preferably straight; saturated, monounsaturated (i.e., one double or triple bond in the chain), or polyunsaturated (i.e., two or more double bonds in the chain; two or more triple bonds in the chain; one or more double and one or more triple bonds in the chain), preferably saturated.

As used herein "topical application" means directly laying on or spreading on outer skin.

As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

As used herein, "hyperpigmented spots" means an excess of pigment in mammalian tissue, or a generalized but spotty increase in melanin pigment of mammalian skin. These are sometimes referred to as age spots, liver spots or freckles.

As used herein, "regulating hyperpigmented spots" means preventing, retarding, arresting, or reversing the process of increased melanin pigment in spots on mammalian skin.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein, "chronic treatment" means continued treatment with an active agent over an extended period during a subject's lifetime, preferably for at least about three weeks, more preferably from about three months to about twenty years, more preferably from about six months to about ten years, more preferably still form about one year to about five years.

As used herein, all percentages are by weight and all measurements are at 25° C. Unless otherwise specified.

Active Compound

The present invention relates to a method for regulating hyperpigmented spots in mammalian skin comprising treating the skin with a safe and effective amount of a composition comprising a salicylic acid active component. The salicylic acid active component can be salicylic acid alone, salicylic acid derivatives and salicylic acid in combination with other active ingredients described below. Most preferred is salicylic acid in a hydroalcoholic solution. The composition for topical application will comprise from about 0.01% to about 50%, preferably from about 0.1% to about 20%, more preferably from about 1% to about 5% of the active compound.

Salicylic acid is a well known active component and is generally described in U.S. Pat. No. 4,514,385 to Damani et al., assigned to Alcon Laboratories, and incorporated herein by reference.

The preferred topical carrier comprises a hydroalcoholic solution at pH 2 to 4 of salicylic acid as the active ingredient together with a cosmetically-acceptable surfactant. The term "cosmetically acceptable surfactant" refers to a surfactant which is not only an effective skin cleanser, but also can be used without undue toxicity, irritation, allergic response, and the like. Furthermore, the surfactant must be capable of being commingled with the active compound in a manner such that there is no interaction which would substantially reduce the efficacy of the composition for regulating hyperpigmented spots. The surfactant component of the compositions of the present invention are selected from anionic, nonionic, zwitterionic, amphoteric and ampholytic surfactants, as well as mixtures of these surfactants. Such surfactants are well-known to those skilled in the detergency art.

More preferably, the salicylic acid active ingredient is a stable, hydroalcoholic composition having a pH value of from 2 to 4 and containing from about 0.2 to about 5.0 percent by weight of sodium methyl cocoyl taurate and/or sodium methyl oleoyl taurate as the anionic surfactant component. Generally, a sufficient amount of a cosmetically acceptable alkaline component (i.e., alkalizing agent) to provide and maintain the composition with a pH from about 2.0 to about 4 is included.

As the alcohol component of the hydroalcoholic solvent, from about 10 to about 60 percent by weight of ethyl alcohol, measured as total $C_2H_5OH$ content, is preferred although a like amount of isopropyl alcohol ($C_3H_7OH$) may also be beneficially utilized. From about 30 to about 80 percent by weight of water is also required as the aqueous component of the hydroalcoholic solvent.

The anionic surfactant component of this active composition, i.e., the taurate surfactant component, is specifically directed to sodium methyl cocoyl taurate and sodium methyl oleoyl taurate, both of which are readily available from diverse commercial suppliers, as noted in The Cosmetic, Toiletry and Fragrance Association (CTFA) Cosmetic Ingredient Dictionary, 3rd Edition, 1982, pages 286–287.

Although it is preferred to use the taurate surfactant as the sole surfactant in the active compositions, other surfactants may be included, the nonionic type having preference over the anionic type in view of the relative non-irritating characteristic to the skin of the former. Cationic type surfactants, which are most irritating to the skin, are less preferred because of their marked susceptibility to hydrolysis at the low acidic pH of the subject compositions.

The pH value of the preferred active component, from about 2 to about 3.5 may be achieved by use of appropriate cosmetically acceptable primary or dual buffer systems. In most instances, the resultant pH of the hydroalcoholic solution of salicylic acid is slightly below or at the lower end of the indicated range, and all that is required to adjust the pH to a desired higher value within the indicated range is to add an alkaline additive such as is commonly utilized in cosmetic formulations for such purpose. Although sodium carbonate is preferred, other suitable alkalizing agents include potassium carbonate, sodium hydroxide, potassium hydroxide, triethanolamine, and the like. If deemed necessary to change or adjust the pH to a lower value, a suitable cosmetically acceptable acidifying agent such as citric acid may be employed.

Pharmaceutical Compositions

In a preferred embodiment, treatment includes the use of a topical pharmaceutical composition comprising the active compound and a pharmaceutically-acceptable carrier. The term "pharmaceutically-acceptable carrier", as used herein, means one or more compatible solid or liquid filler diluents or microencapsulating substances which are suitable for administration to a human or lower animal. Pharmaceutically-acceptable carriers must be of sufficiently high purity and sufficiently low toxicity to render them suitable for administration to the human or lower animal being treated. A safe and effective amount of carrier is from about 50% to about 99.99%, preferably form about 80% to about 99.9%, more preferably from about 95% to about 98% of the composition.

Variations in formulation of these carriers result in a wide variety of products which fall within the scope of the present invention.

The topical pharmaceutical compositions of the present invention may be made into a wide variety of product types. These include, but are not limited to solutions, toilet bars, lotions, creams, beach products, gels, sticks, sprays, pads, ointments, pastes, mousses and cosmetics. These product types may comprise several types of carrier systems including, but not limited to, solutions, emulsions, gels and solids.

The topical pharmaceutical compositions of the present invention formulated as solutions typically include a pharmaceutically-acceptable aqueous or organic solvent. The terms "pharmaceutically-acceptable aqueous solvent" and "pharmaceutically-acceptable organic solvent" refer to a solvent which is capable of having dispersed or dissolved therein the active compound, and possesses acceptable safety properties (e.g., irritation and sensitization characteristics). Water is a typical aqueous solvent. Examples of suitable organic solvents include: propylene glycol, butylene glycol, polyethylene glycol (200–600), polypropylene glycol (425–2025), glycerol, 1,2,4-butanetriol, sorbitol esters, 1,2,-6-hexanetriol, ethanol, isopropanol, butanediol, and mixtures thereof. Preferably, these solutions contain from about 0.01% to about 50% of the active compound, more preferably from about 0.1% to about 20%; and from about 1% to about 80% of an acceptable aqueous or organic solvent, more preferably from about 1% to about 40%.

If the topical pharmaceutical compositions of the present invention are formulated as an aerosol and applied to the skin as a spray-on, a propellant is added to the solution composition. A more complete disclosure of propellants useful herein can be found in Sagarin, *Cosmetics Science and Technology*, 2nd Edition, Vol 2, pp.443–465 (1972).

Topical pharmaceutical compositions of the present invention may be formulated as a solution comprising an emollient. Preferably, such compositions contain from about 0.1% to about 50% of the active compound and from about 2% to about 50% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1. pp. 32–43 (1972), incorporated herein by reference, contains numerous examples of suitable materials.

A lotion can be made from a solution carrier system. Lotions preferably comprise from about 0.1% to about 20%, more preferably from about 1% to about 5%, of the active compound; from about 1% to about 20%, preferably from about 5% to about 10%, of an emollient; and from about 50% to about 90%, preferably from about 60% to about 80%, water.

Another type of product that may be formulated from a solution carrier system is a cream. A cream of the present invention would preferably comprise from about 0.1% to about 20%, more preferably from about 1% to about 5%, of the active compound; from about 5% to about 50%, preferably from about 10% to about 20%, of an emollient, and from about 45% to about 85%, preferably from about 50% to about 75%, water.

Yet another type of product that may be formulated form a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Segarin, *Cosmetics, Science and Technology*, 2nd Edition, Vol. 1, pp. 72–73 (1972).

If the carrier is formulated as an emulsion, from about 1% to about 10%, preferably from about 2% to about 5%, of the carrier system comprises an emulsifier. Emulsifiers may be nonionic, anionic or cationic. Suitable emulsifiers are disclosed in, for example, U.S. Pat. Nos. 3,755,560 to Dickert et al. and 4,421,769 to Dixon et al.; and McCutcheon's *Detergents and Emulsifiers*, North American Edition, pages 371–324 (1986), the disclosures of which are incorporated herein by reference. Preferred emulsifiers are anionic or nonionic, although the other types may also be used.

Lotions and creams can be formulated as emulsions as well as solutions. Preferably such lotions comprise from about 0.1% to about 20%, more preferably from about 1% to about 5%, of the active compound; from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would preferably comprise from about 0.1% to about 20%, more preferably from about 1% to about 5%, of the active compound; from about 1% to about 20%, preferably form about 5% to about 10%, of an emollient; from about 20% to about 80%, preferably from about 30% to about 70%, water; and from about 1% to about 10%, preferably from about 2% to about 5%, of an emulsifier.

Single emulsion skin care preparations, such as lotions and creams, of the oil-in-water type and water-in-oil type are well-known in the cosmetic art and are useful in the present invention. Multiphase emulsion compositions, such as the water-in-oil-in-water type, as disclosed in U.S. Pat. No. 4,254,015 to Fakuda et al., incorporated herein by reference, are also useful in the present invention. In general, such single or multiphase emulsions contain water, emollients and emulsifiers as essential ingredients.

Triple emulsion carrier systems comprising an oil-in-water-in-silicone fluid emulsion composition, as disclosed in U.S. Pat. No. 4,960,764 to Figueroa, are also useful in the present invention. Preferably, this triple emulsion carrier system can be combined with from about 0.1% to about 20%, more preferably from about 1% to about 5%, of the active compound to yield the topical pharmaceutical composition of the present invention.

Another emulsion carrier system useful in the topical pharmaceutical compositions of the present invention is a micro-emulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name TWEENS) or other nonionics; and from about 7% to about 20% water. This carrier system is preferably combined with from about 1% to about 5% of the active compound.

If the topical pharmaceutical compositions of the. present invention are formulated as a gel or a cosmetic stick, a suitable amount of a thickening agent, as disclosed supra, is added to a cream or lotion formulation.

The topical pharmaceutical compositions of the present invention may also be formulated as makeup products such as foundations.

The topical pharmaceutical compositions of the present invention may also be formulated as medicated pads. Suitable examples of these pads are fully disclosed in U.S. Pat. Nos. 4,891,227 and 4,891,228 to Thaman et al., the disclosures of which are incorporated herein.

The topical pharmaceutical compositions of the present invention may contain, in addition to the aforementioned components, a wide variety of additional oil-soluble materials and/or water-soluble materials conventionally used in topical compositions, at their art-established levels.

Various water-soluble materials may also be present in the compositions of this invention. These include humectants, proteins and polypeptides, preservatives and an alkaline agent. In addition, the topical compositions herein can contain conventional cosmetic adjuvants, such as dyes, opacifiers (e.g., titanium dioxide), pigments and perfumes.

The topical pharmaceutical compositions of the present invention may also include a safe and effective amount of a penetration enhancing agent. A preferred amount of penetration enhancing agent is from about 1% to about 5% of the composition. Another useful penetration enhancer for the present invention is the non-ionic polymer under the CTFA designation: polyacrylamide and isoparrafin and laureth-7, available as SEPIGEL from Seppic Corporation. Also useful is polyquaternium-32 and mineral oil known as SALCARE SC92 available from Allied Colloids, Suffolk, Va. This is a class of cationic polymers which are generally described in U.S. Pat. Nos. 4,628,078 to Glover et al. and U.S. Pat. No. 4,599,379 to Flesher et al., both of which are incorporated by reference herein.

Examples of useful penetration enhancers, among others, are disclosed in U.S. Pat. Nos. 4,537,776 to Cooper; U.S. Pat. No. 4,552,872 to Cooper et al.; U.S. Pat. No. 4,557,934 to Cooper; U.S. Pat. No. 4,130,667 to Smith; U.S. Pat. No. 3,989,816 to Rhaadhyaksha; U.S. Pat. No. 4,017,641 to DiGiulio; and European Patent Application 0043738 to Cooper et al., the disclosures of which are incorporated herein by reference.

Other conventional skin care product additives may also be included in the compositions of the present invention. For example, collagen, hyaluronic acid, elastin, hydrolysates, primrose oil, jojoba oil, epidermal growth factor, soybean saponins, mucopolysaccharides, and mixtures thereof may be used.

Local Anesthetic

The present composition preferably includes a local anesthetic selected from benzocaine, lidocaine, procaine, bupivicaine, a eutectic mixture of prilocaine and lignocaine, phenol, diphenhydramine, and the like. Preferably the local anesthetic is present at about 5% to about 30%, and more preferably at about 15% to 25%, by weight, of the composition.

Vitamins

Various vitamins may also be included in the compositions of the present invention. For example, Vitamin A, ascorbic acid, Vitamin B, biotin, panthothenic acid, Vitamin D, Vitamin E, and mixtures thereof and derivatives thereof may be used.

Chelators

In a preferred hyperpigmented spot regulating composition of the present invention, a chelating agent is included as an active agent along with the active compound. As used herein, "chelating agent" means an active agent capable of removing a metal ion from a system by forming a complex so that the metal ion cannot readily participate in or catalyze chemical reactions. The inclusion of a chelating agent increases the hyperpigmented spot regulating benefits of the composition.

The chelating agent is present in the compositions of the present invention at preferably from about 0.1% to about 10%, more preferably from about 1% to about 5%, by weight. Preferred chelators useful in compositions of the present invention are furildioxime and derivatives thereof, more preferably amphi-2-furildioxime.

Skin Protectants

In a preferred hyperpigmented spot composition of the present invention, a safe and effective amount of a skin protectant may be added. The skin protectant preferably comprises from about 0.001% to about 2%, more preferably from about 0.01% to about 1% of the composition. Useful skin protectants are disclosed in the *Federal Register* Vol. 48, No. 32 and include allantoin, aluminum hydroxide gel, bismuth subnitrate, boric acid, calamine, cocoa butter, corn starch, dimethicone, glycerin, kaolin, live yeast cell derivative, petrolatum, shark liver oil, sodium bicarbonate, sulfur, tannic acid, white petrolatum, zinc acetate, zinc carbonate, zinc oxide, and mixtures thereof.

Other useful components include hormones such as pregnenolone and estrogens. Also useful are the alpha-, or beta-hydroxy acids or alpha-keto acids or derivatives thereof, as disclosed in U.S. Pat. No. 4,234,599 to Van Scott et al., which is incorporated by reference herein. Useful members of this class include alpha-hydroxy-butyric acid, alpha-hydroxyisobutyric acid, alpha-hydroxyisocaproic acid, alpha-hydroxyisovaleric, atrolactic acid, beta-hydroxybutyric acid, beta-phenyl lactic acid, beta-phenylpyruvic acid, citric acid ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, lactic acid, malic acid, amndelic acid, emthyl pyruvate, mucic acid, pyruvic acid, saccharic acid, saccharic acid 1,4-lactone, tartaric acid and tartronic acid.

Methods for Regulating Hyperpimented Spots Mammalian Skin

The present invention relates to a method for regulating hyperpigmented spots in mammalian skin. Such a method comprises treating the skin with a safe and effective amount of the active compound. The amount of active compound and frequency of treatment will vary widely depending upon the level of hyperpigmented spots already in existence in the subject, the rate of further hyperpigmented spots formation, and the level of regulation desired.

An agent may also be added to any of the compositions of the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. Nos. 4,663,157 to Brock, which is incorporated herein by reference.

A preferred method of treating the skin is via chronic topical application of a safe and effective amount of the active compound to regulate hyperpigmented spots in mammalian skin. The amount of active compound and frequency of topical application to the skin can vary widely, depending upon personal needs, but it is suggested as an example that topical application range from about once per week to about 10 times daily, preferably from about twice per week to about 4 times daily, more preferably from about 3 times a week to about 3 times daily, most preferably about once or twice per day.

By "chronic" application, it is meant herein that the period of topical application may be over the lifetime of the subject, preferably for a period of at least about three weeks, more preferably from about three months to about twenty years, more preferably from about six months to about ten years, more preferably still from about one year to about five years, thereby resulting in regulation of hyperpigmented spots in mammalian skin.

A preferred method of the present invention for regulating hyperpigmented spots in mammalian skin involves applying both a safe and effective amount of the active compound and a safe and effective amount of one or more of a Vitamin, chelating agent, and skin protectant to the skin simultaneously. As used herein, "simultaneous application" or "simultaneously" means applying the agents to the skin at the same situs on the body at about the same time. Though this can be accomplished by applying the agents separately to the skin, preferably a composition comprising all the desired agents commingled is applied to the skin. The amount of chelating agent generally applied is from about 0.001 mg to about 1.0 mg, preferably form about 0.01 mg to about 0.5 mg, more preferably from about 0.05 mg to about 0.1 mg per $cm^2$ skin. The amount of active compound applied is generally from about 0.001 mg to about 1.0 mg per $cm^2$ skin per application, preferably from about 0.01 mg to about 0.5 mg per $cm^2$, more preferably from about 0.05 to about 0.25 mg/$cm^2$ skin per application.

In a preferred hyperpigmented spot treatment composition of the present invention, compositions comprise one, a combination or all of a Vitamin, chelating agent and skin protectant included as actives along with the active compound. The inclusion of any, a combination or all of these agents with the active compound increases the hyperpigmented spot treatment benefits of the composition.

It is appreciated that various modifications to the inventive concepts described herein may be apparent to those skilled in the art without departing from the spirit and scope of the present invention defined by the hereinafter appended claims.

What is claimed is:

1. A method for treating hyperpigmented spots in mammalian skin, comprising the steps of:
    (a) identifying a hyperpigmented spot on the mammalian skin;
    (b) providing a composition comprising a safe and effective amount of salicylic acid, a surfactant, and a pharmaceutically-acceptable carrier; and
    (c) applying the composition to the hyperpigmented spot at a frequency of about once per week to about ten times daily thereby significantly inducing a positive modification in the hyperpigmented spot.

2. The method of claim 1 wherein the salicylic acid is present in the composition at about 0.01% to about 50%, by weight.

3. The method of claim 1 wherein the salicylic acid is present in the composition at about 0.1% to about 20%, by weight.

4. The method of claim 1 wherein the salicylic acid is present in the composition at about 1% to about 5%, by weight.

5. The method of claim 1 wherein the composition is a hydroalcoholic solution at a pH of 2 to 4.

6. The method of claim 1 wherein the surfactant is selected from the group consisting of and an anionic surfactant, and mixtures thereof a nonionic surfactant, a cationic surfactant, a zwitterionic surfactant, an amphoteric surfactant, an ampholytic surfactant, and mixtures thereof.

7. The method of claim 1 wherein the surfactant is selected from sodium methyl cocoyl taurate and sodium methyl oleoyl taurate.

8. The method of claim 1 further including an ingredient selected from the group consisting of a local anesthetic, a vitamin, a chelator and a skin protectant.

9. The method of claim 8 wherein the local anesthetic is selected from the group consisting of benzocaine, lidocaine, procaine, bupivicaine, a eutectic mixture of prilocaine and lignocaine, phenol, diphenhydramine, and mixtures thereof.

10. The method of claim 8 wherein the local anesthetic is present in the composition at about 5% to about 30%, by weight.

11. The method of claim 1 wherein the pharmaceutically-acceptable carrier as a topical carrier.

12. The method of claim 11 wherein the topical carrier comprises:

a) from about 10 to about 60 weight percent of $C_2H_5OH$ or $C_3H_7OH$;
b) from about 30 to about 80 weight percent of water; and
c) from about 0.2 to about 5.0 weight percent of sodium methyl cocoyl taurate or sodium methyl oleoyl taurate the composition having a pH value of from about 2 to about 3.5.

13. The method of claim 1 wherein the pharmaceutically-acceptable carrier is a topical substance selected from the group consisting of an aerosol, a lotion, a cream, an ointment, a gel, a cosmetic, a makeup foundation and a medicated pads.

* * * * *

UNITED STATES PATENT AND TRADEMARK OFFICE
CERTIFICATE OF CORRECTION

PATENT NO.     : 6,485,714 B1
DATED          : November 26, 2002
INVENTOR(S)    : Bradford et al.

It is certified that error appears in the above-identified patent and that said Letters Patent is hereby corrected as shown below:

<u>Title page,</u>
Item [75], "Mangione" should be -- Bradford --

<u>Column 8,</u>
Line 47, "and" should be deleted
Line 48, "and mixtures thereof" should be deleted Signed and Sealed this First Day of April, 2003

JAMES E. ROGAN
*Director of the United States Patent and Trademark Office*